US012636184B2

(12) United States Patent
     Trauthen

(10) Patent No.: US 12,636,184 B2
(45) Date of Patent: May 26, 2026

(54) SCHLEMM'S CANAL DRUG ELUTING DEVICE AND METHOD

(71) Applicant: Alcon Inc., Fribourg (CH)

(72) Inventor: Brett A. Trauthen, Newport Beach, CA (US)

(73) Assignee: Alcon Inc., Fribourg (CH)

( * ) Notice: Subject to any disclaimer, the term of this patent is extended or adjusted under 35 U.S.C. 154(b) by 642 days.

(21) Appl. No.: 18/150,323

(22) Filed: Jan. 5, 2023

(65) Prior Publication Data

US 2023/0210693 A1    Jul. 6, 2023

Related U.S. Application Data

(60) Provisional application No. 63/297,133, filed on Jan. 6, 2022.

(51) Int. Cl.
     *A61F 9/00*     (2006.01)
     *A61F 2/94*     (2013.01)
     *A61F 9/007*    (2006.01)

(52) U.S. Cl.
     CPC .............. *A61F 9/0017* (2013.01); *A61F 2/94* (2013.01); *A61F 9/00781* (2013.01); *A61F 2210/0004* (2013.01)

(58) Field of Classification Search
     CPC ...... A61F 9/00781; A61F 2/94; A61F 9/0017; A61F 2210/0004; A61F 2009/00891; A61F 2250/0067; A61F 2250/0068; A61K 9/0051; A61M 2210/0612; A61M 27/002
     See application file for complete search history.

(56) References Cited

U.S. PATENT DOCUMENTS

| | | | |
|---|---|---|---|
| 6,007,510 | A | 12/1999 | Nigam |
| 6,142,969 | A | 11/2000 | Nigam |
| 6,450,984 | B1 | 9/2002 | Lynch |
| 6,689,085 | B1 | 2/2004 | Rubenstein |
| 6,881,197 | B1 | 4/2005 | Nigam |
| 7,220,238 | B2 | 5/2007 | Lynch |
| 7,355,216 | B2 | 4/2008 | Yang |
| 9,510,973 | B2 | 12/2016 | Wardle |
| 9,554,940 | B2 | 1/2017 | Haffner et al. |

(Continued)

FOREIGN PATENT DOCUMENTS

| | | | | |
|---|---|---|---|---|
| CN | 107530190 A | 1/2018 | | |
| WO | WO-2010135369 A1 * | 11/2010 | ........... | A61F 9/0017 |

(Continued)

OTHER PUBLICATIONS

Li Shasha, et al., Progress on microsponge for drug delivery system, Chinese journal of experimental traditional medical formulae, vol. 18, No. 2, 244-246, 2011.

(Continued)

*Primary Examiner* — Wesley G Harris

(57)    ABSTRACT

A method of delivering a pharmaceutical composition to Schlemm's canal of an eye is disclosed. The method may comprise inserting a drug delivery device in conjunction with a microstent into Schlemm's canal. The drug delivery device may comprise a bioerodable polymer and a pharmaceutical composition, and the drug delivery device may be configured to erode over time and to elute the pharmaceutical composition into aqueous humor within Schlemm's canal as it erodes.

7 Claims, 1 Drawing Sheet

(56) References Cited

U.S. PATENT DOCUMENTS

| | | | |
|---|---|---|---|
| 12,029,683 | B2 | 7/2024 | Blanda et al. |
| 2002/0026200 | A1 | 2/2002 | Savage |
| 2003/0167031 | A1 | 9/2003 | Odland |
| 2003/0175324 | A1 | 9/2003 | Robinson et al. |
| 2003/0220603 | A1 | 11/2003 | Lynch |
| 2003/0236483 | A1 | 12/2003 | Ren |
| 2004/0210185 | A1 | 10/2004 | Tu |
| 2004/0225250 | A1 | 11/2004 | Yablonski |
| 2005/0277864 | A1 | 12/2005 | Haffner |
| 2005/0277912 | A1 | 12/2005 | John |
| 2005/0283108 | A1 | 12/2005 | Savage |
| 2006/0015089 | A1 | 1/2006 | Meglin |
| 2006/0093642 | A1 | 5/2006 | Ranade |
| 2006/0173397 | A1 | 8/2006 | Tu |
| 2006/0200113 | A1* | 9/2006 | Haffner ............... A61F 9/00781 |
| | | | 606/6 |
| 2006/0204738 | A1 | 9/2006 | Dubrow |
| 2007/0276316 | A1 | 11/2007 | Haffner |
| 2007/0282247 | A1 | 12/2007 | Desai |
| 2007/0293807 | A1 | 12/2007 | Lynch |
| 2008/0009781 | A1 | 1/2008 | Anwar |
| 2008/0015488 | A1 | 1/2008 | Tu |
| 2008/0039768 | A1 | 2/2008 | Francis |
| 2008/0051691 | A1 | 2/2008 | Dragoon |
| 2008/0125838 | A1 | 5/2008 | Francis |
| 2009/0082863 | A1* | 3/2009 | Schieber ............... A61F 9/0017 |
| | | | 623/6.13 |
| 2009/0104248 | A1 | 4/2009 | Rapacki et al. |
| 2010/0114309 | A1 | 5/2010 | De, Jr. et al. |
| 2011/0105990 | A1* | 5/2011 | Silvestrini ........... A61F 9/00781 |
| | | | 604/8 |
| 2011/0144559 | A1 | 6/2011 | Lafdi |
| 2011/0238075 | A1* | 9/2011 | Clauson ............... A61K 9/0051 |
| | | | 606/107 |
| 2011/0319806 | A1 | 12/2011 | Wardle |
| 2012/0035524 | A1* | 2/2012 | Silvestrini ........... A61F 9/00781 |
| | | | 604/8 |
| 2012/0310137 | A1 | 12/2012 | Silvestrini |
| 2012/0323159 | A1 | 12/2012 | Wardle et al. |
| 2013/0184631 | A1 | 7/2013 | Pinchuk |
| 2013/0231603 | A1 | 9/2013 | Wardle et al. |
| 2014/0213958 | A1* | 7/2014 | Clauson ............. A61F 9/00781 |
| | | | 604/8 |
| 2014/0243729 | A1* | 8/2014 | Rynerson ............ A61F 9/00781 |
| | | | 604/8 |
| 2014/0248454 | A1 | 9/2014 | Lafdi |
| 2014/0249463 | A1 | 9/2014 | Wardle et al. |
| 2017/0164831 | A1 | 6/2017 | Choo et al. |
| 2017/0281409 | A1 | 10/2017 | Haffner et al. |
| 2018/0280194 | A1* | 10/2018 | Heitzmann ........ A61K 31/5377 |
| 2020/0121503 | A1* | 4/2020 | Badawi ................. A61F 9/0017 |
| 2020/0261271 | A1* | 8/2020 | Horvath .................. A61L 27/54 |
| 2021/0030590 | A1 | 2/2021 | Blanda et al. |
| 2021/0212858 | A1 | 7/2021 | Tran et al. |
| 2021/0330499 | A1 | 10/2021 | Wardle et al. |
| 2022/0054314 | A1 | 2/2022 | Van Meter et al. |

FOREIGN PATENT DOCUMENTS

| | | | | |
|---|---|---|---|---|
| WO | WO-2014190029 | A1 * | 11/2014 | ......... A61F 9/00781 |
| WO | 2015085251 | A1 | 6/2015 | |
| WO | 2015108970 | A1 | 7/2015 | |
| WO | 2016159999 | A1 | 10/2016 | |
| WO | 2017106517 | A1 | 6/2017 | |

OTHER PUBLICATIONS

Liu Junling, et al., Application Research Progress of Porous Materials in Drug Delivery, Guangzhou Chemical Industry, vol. 41 No. 13, 42-43, 2013.

* cited by examiner

SCHLEMM'S CANAL DRUG ELUTING DEVICE AND METHOD

INCORPORATION BY REFERENCE

All publications and patent applications mentioned in this specification are herein incorporated by reference in their entirety to the same extent as if each individual publication or patent application was specifically and individually indicated to be incorporated by reference.

TECHNICAL FIELD

The invention set forth in the appended claims relates generally to surgical implants, such as ophthalmic devices, including, without limitation, ophthalmic drug delivery devices.

BACKGROUND

Glaucoma is an ocular condition resulting in a potentially damaging increase in intraocular pressure. Glaucoma drug therapies are often directed to reducing the production of aqueous humor in an effort to reduce intraocular pressure. Glaucoma surgical therapies target the aqueous humor outflow path from the anterior chamber through the trabecular meshwork to Schlemm's canal where it then flows out of the eye via outflow channels and the episcleral veins. In addition, while there are drugs that can dilate the outflow channels and/or episcleral veins, there are currently no efficient ways to deliver those drugs at a sufficient concentration over a sufficient period of time to provide enough dilation of the outflow channels and/or episcleral veins to reduce intraocular pressure.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise a method of delivering a pharmaceutical composition to Schlemm's canal of an eye. The method may comprise inserting a drug delivery device into Schlemm's canal, inserting a microstent comprising an open central channel bordered in part by one or more wall supports into Schlemm's canal, supporting a longitudinal section of Schlemm's canal with the microstent, and allowing the drug delivery device to erode over time. The drug delivery device may comprise a bioerodable polymer and the pharmaceutical composition, and the drug delivery device may erode over time to elute the pharmaceutical composition into aqueous humor within Schlemm's canal as it erodes. The method may further comprise dilating one or more of an outflow channel and an episcleral vein with the pharmaceutical composition.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Drugs that dilate the outflow channels and episcleral veins downstream of Schlemm's canal can help lower intraocular pressure. The flow of aqueous humor from the anterior chamber to and through Schlemm's canal can be enhanced by the use of Schlemm's canal microstents, such as those described in U.S. Pat. Nos. 7,740,604; 8,337,509; 8,425,449; and 8,512,404. One aspect of the present invention is a combination of a Schlemm's canal microstent and a time-release drug delivery device disposed in Schlemm's canal downstream of the microstent to more effectively deliver a drug to the outflow channels and episcleral veins over an extended period of time.

Figure 1:
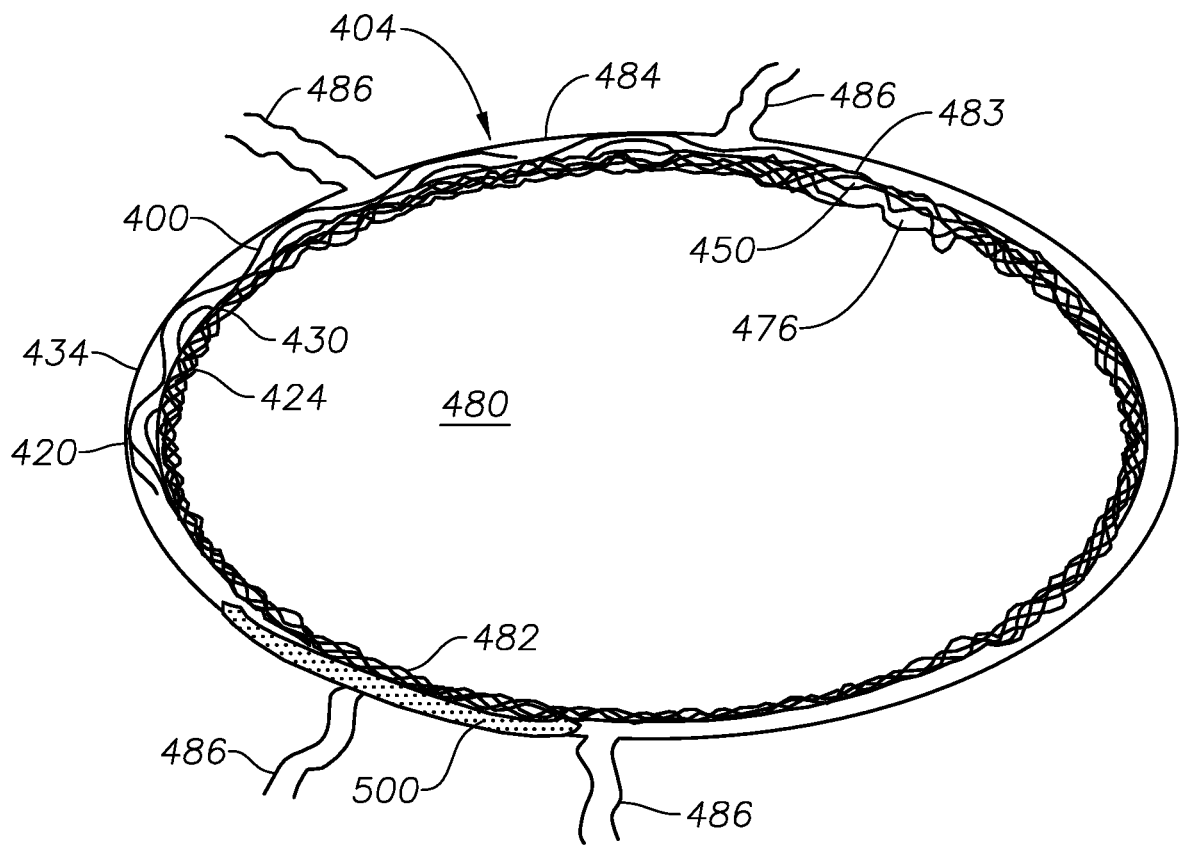
FIG. 1 shows a drug delivery device according to this invention in Schlemm's canal near a microstent.

FIG. 1 shows an exemplary ocular microstent 400 with its body portion 404 disposed in Schlemm's canal 484 and its inlet 450 disposed in the anterior chamber 480. As shown, the body of microstent 400 has pairs of struts 420, openings 430, spine areas 424, and an open channel 434 extending along the body portion and having an open side facing the outflow channels. Microstent 400 may be inserted into Schlemm's canal 484 from the anterior chamber 480 through an opening 483 in the trabecular meshwork 482 so that an inlet portion 450 remains in the anterior chamber 480. When in place in Schlemm's canal, microstent 400 supports the walls of Schlemm's canal so that aqueous humor can flow from the anterior chamber 480 through a channel 476 in the inlet portion 450, and/or through the trabecular meshwork 482 and openings 430, into the open channel 434 of the microstent body and then into collector channels 486, which lead to episcleral veins (not shown). In some embodiments, microstent 400 supports at least a 4 mm longitudinal length of Schlemm's canal, at least a 6 mm length of Schlemm's canal, or at least an 8 mm length of Schlemm's canal. Microstent 400 may be, e.g., one of the implants disclosed in U.S. Pat. Nos. 7,740,604; 8,337,509; 8,425,449; 8,512,404, all of which are incorporated by reference in their entireties; or any other suitable Schlemm's canal microstent. Microstent 400 may be fabricated from one or more biocompatible materials possessing the necessary structural and mechanical attributes. Both metallic and non-metallic materials may be suitable. Examples of suitable metallic materials may include stainless steel, tantalum, gold, titanium, and nickel-titanium alloys known in the art as Nitinol. For example, Nitinol is commercially available from Memry Technologies (Brookfield, Conn.), TiNi Alloy Company (San Leandro, Calif.), and Shape Memory Applications (Sunnyvale, Calif.).

Figure 2:
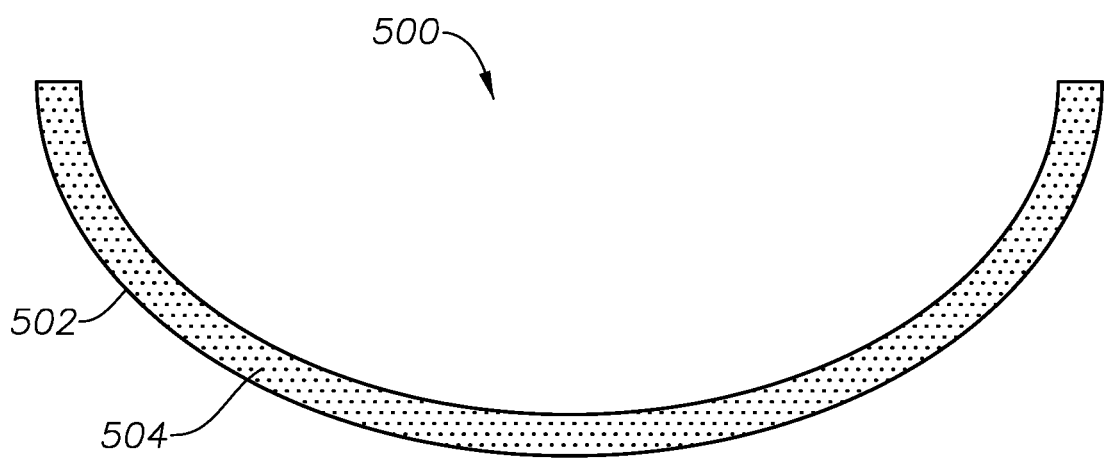
FIG. 2 shows the drug delivery device of FIG. 1.

FIG. 1 also shows a drug delivery device 500 disposed in Schlemm's canal near microstent 400. As shown in FIG. 2, drug delivery device 500 is formed from a bioerodable polymer 502, such as Poly(lactic-co-glycolic acid) (PLGA) or Polyethylene glycol (PEG), or a blend thereof. Additional suitable bioerodable or bioresorbable polymers and copolymers may be derived from monomers such as glycolide, glycolic acid, lactide, lactic acid, caprolactone, dioxanone, trimethylene carbonate, and combinations thereof. In some instances, the bioerodable polymer 502 may additionally or alternatively comprise amorphous or semicrystalline forms of such polymers. A drug that causes the collector channels and episcleral veins to dilate is compounded with the bioerodable polymer of the drug delivery device to form pockets 504 of the drug so that, as the drug delivery device 500 bioerodes, the drug elutes into the aqueous humor flowing to the collector channels. Suitable drugs include rho kinase inhibitors and K(ATP) channel blockers such as cromakalim.

In some embodiments, drug delivery device 500 is 6-8 mm long with a diameter of 7-10 mm. In some embodiments, drug delivery device 500 is curved, as shown in FIG. 2, to match the curve of Schlemm's canal. In other embodiments, drug delivery device 500 is flexible and conforms to the curve of Schlemm's canal.

Drug delivery device 500 may be delivered into Schlemm's canal through the same opening in the trabecular meshwork that is used to place the microstent. In some embodiments, Schlemm's canal may be dilated prior to placement of the drug delivery device or the microstent, such as by delivering pressurized viscoelastic material into Schlemm's canal. For example, Schlemm's canal may be dilated with viscoelastic material by using an OMNI® Surgical System or by using the one of devices described in U.S. Appl No. 63/236,598.

In some embodiments, drug delivery device 500 is placed closed enough to the microstent (e.g., within 1-3 mm of the distal end of microstent 400) so as to be within a flow of aqueous humor from the microstent so that the device 500 will erode and deliver the drug to the flowing aqueous humor. In some embodiments, the drug delivery device erodes and delivers the drug over an extended period of time, e.g., many months or even years.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

6

What is claimed is:

1. A method of delivering a pharmaceutical composition to Schlemm's canal of an eye, the method comprising:
inserting a drug delivery device through an opening in trabecular meshwork into Schlemm's canal, the drug delivery device comprising a bioerodable polymer and the pharmaceutical composition, the drug delivery device being configured to erode over time and to elute the pharmaceutical composition into aqueous humor within Schlemm's canal as it erodes;
inserting a microstent into Schlemm's canal, the microstent comprising an open central channel bordered in part by one or more wall supports, wherein inserting the microstent comprises inserting the microstent from an anterior chamber of the eye through the opening in the trabecular meshwork;
supporting at least 4 mm of a longitudinal section of Schlemm's canal with the microstent; and
allowing the drug delivery device to erode over time to elute the pharmaceutical composition into aqueous humor within Schlemm's canal as it erodes to dilate one or more of an outflow channel and an episcleral vein with the pharmaceutical composition.

2. The method of claim 1, wherein the drug delivery device is inserted into Schlemm's canal before the microstent is inserted into Schlemm's canal.

3. The method of claim 1, wherein the drug delivery device is inserted into Schlemm's canal after the microstent is inserted into Schlemm's canal.

4. The method of claim 1, wherein the step of inserting the drug delivery device comprises placing the drug delivery device within 3-6 mm of the microstent in Schlemm's canal.

5. The method of claim 1, further comprising dilating Schlemm's canal before inserting the microstent or the drug delivery device into Schlemm's canal.

6. The method of claim 5, wherein the step of dilating Schlemm's canal comprises injecting a substance into Schlemm's canal.

7. The method of claim 6, wherein the substance is a viscoelastic material.

* * * * *